(12) United States Patent
Krioutchkov et al.

(10) Patent No.: US 8,659,293 B2
(45) Date of Patent: Feb. 25, 2014

(54) MULTI-PHASE METERING DEVICE FOR OILFIELD APPLICATIONS

(75) Inventors: Serguei I. Krioutchkov, Calgary (CA); Apostolos Kantzas, Calgary (CA); Zhengyin Wang, Calgary (CA)

(73) Assignee: Perm Instruments Inc., Calgary, Alberta (CA)

( * ) Notice: Subject to any disclaimer, the term of this patent is extended or adjusted under 35 U.S.C. 154(b) by 270 days.

(21) Appl. No.: 13/192,389

(22) Filed: Jul. 27, 2011

(65) Prior Publication Data

US 2012/0092008 A1 Apr. 19, 2012

(30) Foreign Application Priority Data

Oct. 13, 2010 (CA) .................................... 2717541

(51) Int. Cl.
*G01V 3/00* (2006.01)
(52) U.S. Cl.
USPC .......................................................... 324/307
(58) Field of Classification Search
USPC .................................................. 324/300–322
See application file for complete search history.

(56) References Cited

U.S. PATENT DOCUMENTS

| | | | |
|---|---|---|---|
| 4,350,955 A | 9/1982 | Jackson et al. | |
| 5,990,417 A * | 11/1999 | Senda et al. | 174/391 |
| 6,157,276 A * | 12/2000 | Hedeen et al. | 335/216 |
| 6,346,813 B1 | 2/2002 | Kleinberg | |
| 6,825,657 B2 | 11/2004 | Kleinberg et al. | |
| 6,844,492 B1 * | 1/2005 | Wang et al. | 174/36 |
| 6,846,985 B2 * | 1/2005 | Wang et al. | 174/391 |
| 6,952,096 B2 | 10/2005 | Freedman | |
| 7,053,611 B2 | 5/2006 | Freedman | |
| 7,091,719 B2 | 8/2006 | Freedman | |
| 7,463,027 B2 | 12/2008 | Prammer et al. | |
| 7,643,027 B2 | 1/2010 | Rothstein et al. | |
| 7,777,489 B2 * | 8/2010 | Kawamoto | 324/318 |
| 8,411,394 B2 * | 4/2013 | Sato | 360/324 |
| 8,487,727 B2 * | 7/2013 | Wu et al. | 335/216 |
| 2004/0254419 A1 * | 12/2004 | Wang et al. | 600/8 |
| 2005/0025797 A1 * | 2/2005 | Wang et al. | 424/422 |
| 2005/0079132 A1 * | 4/2005 | Wang et al. | 424/1.11 |
| 2007/0222444 A1 | 9/2007 | Reiderman | |
| 2009/0072825 A1 | 3/2009 | Prammer et al. | |
| 2009/0128144 A1 | 5/2009 | Freedman et al. | |
| 2010/0001730 A1 | 1/2010 | Stephenson et al. | |

\* cited by examiner

*Primary Examiner* — Dixomara Vargas
(74) *Attorney, Agent, or Firm* — Sheppard, Mullin, Richter & Hampton LLP

(57) ABSTRACT

This application is related to a system and methods for sampling fluids and gases using nuclear magnetic resonance (NMR) technology. Specifically the system is related to an improved metallic pipe design for use at oil and gas well heads that includes integral coils for transmitting an NMR pulse sequence and detecting NMR signals and can be used as a component of an NMR instrument. The methods are related to obtaining and analyzing NMR spectra in stationary and flowing states.

22 Claims, 7 Drawing Sheets

MULTI-PHASE METERING DEVICE FOR OILFIELD APPLICATIONS

FIELD OF THE INVENTION

This application is related to a system and methods for sampling fluids and gases using nuclear magnetic resonance (NMR) technology. Specifically the system is related to a robust field oriented NMR system and an improved metallic pipe design for use at oil and gas well heads that includes integral coils for transmitting an NMR pulse sequence and detecting NMR signals and can be used as a component of an NMR instrument. The methods are related to obtaining and analyzing NMR spectra in stationary and flowing states.

BACKGROUND OF THE INVENTION

In the oil and gas industry, production well-testing at oil and gas wellheads is performed to quantify the amount of water, oil and gas produced from an individual well. This information is important as it allows the parameters of oil production to be adjusted in order to maximize the efficiency of the production well. Conventional well testing technologies, such as Test Separators and Dean Stark extraction, generally involve the use of large scale and expensive equipment that is time-consuming to use and that, as a result of the complexity of the equipment, often leads to delays during well production. Alternative metering technologies, such as Nuclear Magnetic Resonance (NMR), Microwaves, and Gamma Ray based meters, are becoming increasingly available and generally have the potential to offer savings in terms of time, space, and cost in comparison to conventional well testing technologies. In addition, these alternative metering technologies typically have the capability to be more reliable and accurate compared to conventional well testing technologies. A magnetic resonance apparatus is described in U.S. Pat. No. 4,350,955.

In general, conventional pipes used to convey hydrocarbon fluids from wells have a metallic component to them. Metallic pipes are known to create problems for certain alternative metering technologies, such as nuclear magnetic resonance (NMR) meters. NMR meters function by applying an external static magnetic and a pulsating electromagnetic field to a sample to determine the components of the sample in terms of water, oil and gas content. Such systems are described in US Patent Publication No. 2009/0128144; US Patent Publication No. 2009/0072825; U.S. Pat. No. 6,346,813; U.S. Pat. No. 7,463,027; US Patent Publication No. 2010/0001730; and U.S. Pat. No. 6,825,657. As NMR meters use magnetic fields, metallic materials located near NMR meters will serve as transmitters and undermine the accuracy and sensitivity of the NMR meter. As such, there is generally a need for systems that mitigate these problems, and more specifically there has been a need for improved pipe designs that can be used with an NMR metering tool to increase the accuracy and sensitivity of an NMR meter in the field.

In addition, the oil and gas industry generally operates in a high pressure, temperature and corrosive environment where process fluids are typically comprised of hydrocarbons, hydrogen sulfide, water, steam, carbon dioxide and inert substances such as nitrogen gas and sand particles. As is known, high temperatures and pressures are routinely encountered in a production well, with temperatures reaching 533 K (260° C.; 500° F.) and pressures reaching 4136 kPa (600 Psi). Thus, in the context of alternate metering technologies, including NMR equipment, there continues to be a need for effective apparatus for containing a fluid sample at well head that can withstand the corrosive environment of oil and gas wells as well as the high temperatures and pressures of oil and gas wells while also enabling effective alternative metering technologies.

A review of the prior art indicates that such systems and particularly NMR systems have not been developed. For example, U.S. Pat. No. 7,053,611; U.S. Pat. No. 7,091,719; U.S. Pat. No. 6,952,096 and US Patent Publication No. 2007/0222444 describe methods for determining fluid properties in formations using NMR instruments.

As a result, there continues to be a need for well-testing equipment and methodologies, particularly for NMR instruments, that improve the effectiveness of NMR measurements in both stationary and moving fluids and can be performed in a short period of time in the field.

SUMMARY OF THE INVENTION

In accordance with the invention, there is provided a pipe system for enabling nuclear magnetic resonance (NMR) analysis of gas and liquids within the pipe system comprising: an inner layer defining an internal volume within the pipe system; an insulating layer in operative contact with the inner layer, the insulating layer containing and supporting an NMR resonator coil; a shielding layer in operative contact with the insulating layer; and an outer non-magnetic layer in operative contact with the shielding layer for operatively containing pressurized fluids within the inner layer.

In further embodiments, the outer non-magnetic layer is selected from any one of or a combination of titanium, stainless steel, beryllium, and copper. In a preferred embodiment, the outer non-magnetic layer is titanium.

In yet another embodiment, the ratio of the diameter of the NMR resonator coil and the diameter of the shielding layer ($D_R/D_{SL}$) is between 0.3 and 0.7.

In other embodiments, the shielding layer is selected from any one of or a combination of silver, copper, titanium and a super conductor. If the shielding layer is copper, it is preferred the ratio of the diameter of the NMR resonator coil and the diameter of the shielding layer ($D_R/D_{SL}$) is 0.5-0.6. If the shielding layer is titanium, it is preferred the ratio of the diameter of the NMR resonator coil and the diameter of the shielding layer ($D_R/D_{SL}$) is 0.3-0.4.

In various embodiments, the insulating layer is a resin and/or a thermoplastic such as polyetheretherketone (PEEK).

In one embodiment, the resonator coil is copper. In another embodiment, the resonator coil is the same material as the shielding layer. In another embodiment, the insulating layer has a higher conductivity than the resonator coil.

In other embodiments, the inner layer is polyetheretherketone (PEEK) or Teflon®.

In another embodiment, the length of the resonator coil along the pipe is greater than twice the diameter of the resonator coil.

In one embodiment, the resonator coil comprises a plurality of coils connected in parallel.

In another aspect, the invention provides a nuclear magnetic resonance system comprising: a low field (1-5 MHz) permanent magnet operatively configured to an NMR pipe system; a pulse signal creation circuit operatively connected to the resonator coil for generating radiofrequency (RF) pulsations to the resonator coil; a RF receiver circuit for receiving and filtering RF data from the pipe system for delivery to a data acquisition system; a transceiver switch circuit operatively connected to the pulse signal creation circuit and RF receiver circuit for operative switching between a signal creation and a signal listening mode; and an explosion proof container for operative containment of the magnet, pulse signal creation and RF receiver circuit and transceiver circuit. The system may also include an air purge cooling system for maintaining a positive pressure within the explosion proof container.

In yet another aspect, the invention provides a method of measuring the relative quantity of a gas or liquid in a high temperature and pressure fluid using nuclear magnetic resonance (NMR) relaxometry in an NMR pressure tube, comprising the steps of: a) calibrating the NMR pressure tube with a pure water sample; b) calibrating the NMR pressure tube with a pure oil sample; c) repeating steps a) and b) over a selected temperature range; d) introducing at least a two-component mixture into the NMR pressure tube; e) measuring relaxation curves of a hydrogen signal; and f) calculating water-cut based on relaxation spectra obtained from relaxation curves of step e). The two-component mixture may be stationary or be flowing within the NMR pressure tube.

BRIEF DESCRIPTION OF THE DRAWINGS

The invention is described with reference to the accompanying figures in which.

DETAILED DESCRIPTION OF THE INVENTION

With reference to the figures, an NMR-compatible system 10 for use with an NMR instrument 12 and methods for determining the content of a fluid at oil and gas well heads using the NMR-compatible system and NMR instrument are described.

NMR-Compatible Apparatus

Figure 3:
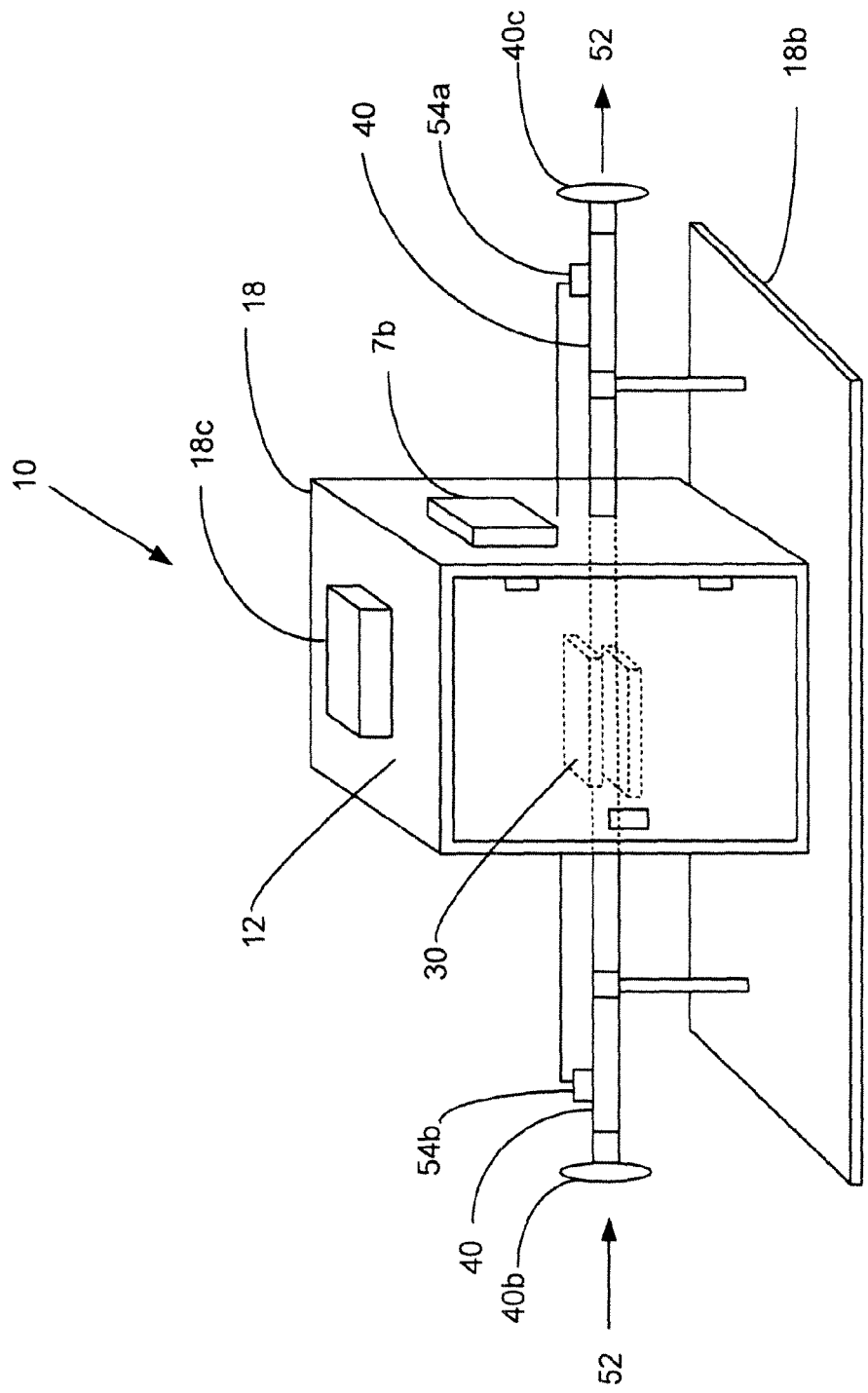
FIG. 3 is a front sectional view of an NMR apparatus in accordance with one embodiment of the invention.

As shown in FIG. 3, the NMR-compatible system 10 consists of an NMR pipe 40 that is connected to conventional well-head piping (not shown). The NMR pipe 40 has connection devices 40b, 40c at each end to secure the pipe to the conventional pipe. A portion of or all fluid from the conventional pipe is diverted through the NMR pipe 40 in a one-way direction, as shown in FIG. 3, wherein the fluid within the NMR pipe is subjected to NMR measurement by the NMR instrument 12 to determine the content of the fluid sample.

Figure 1:
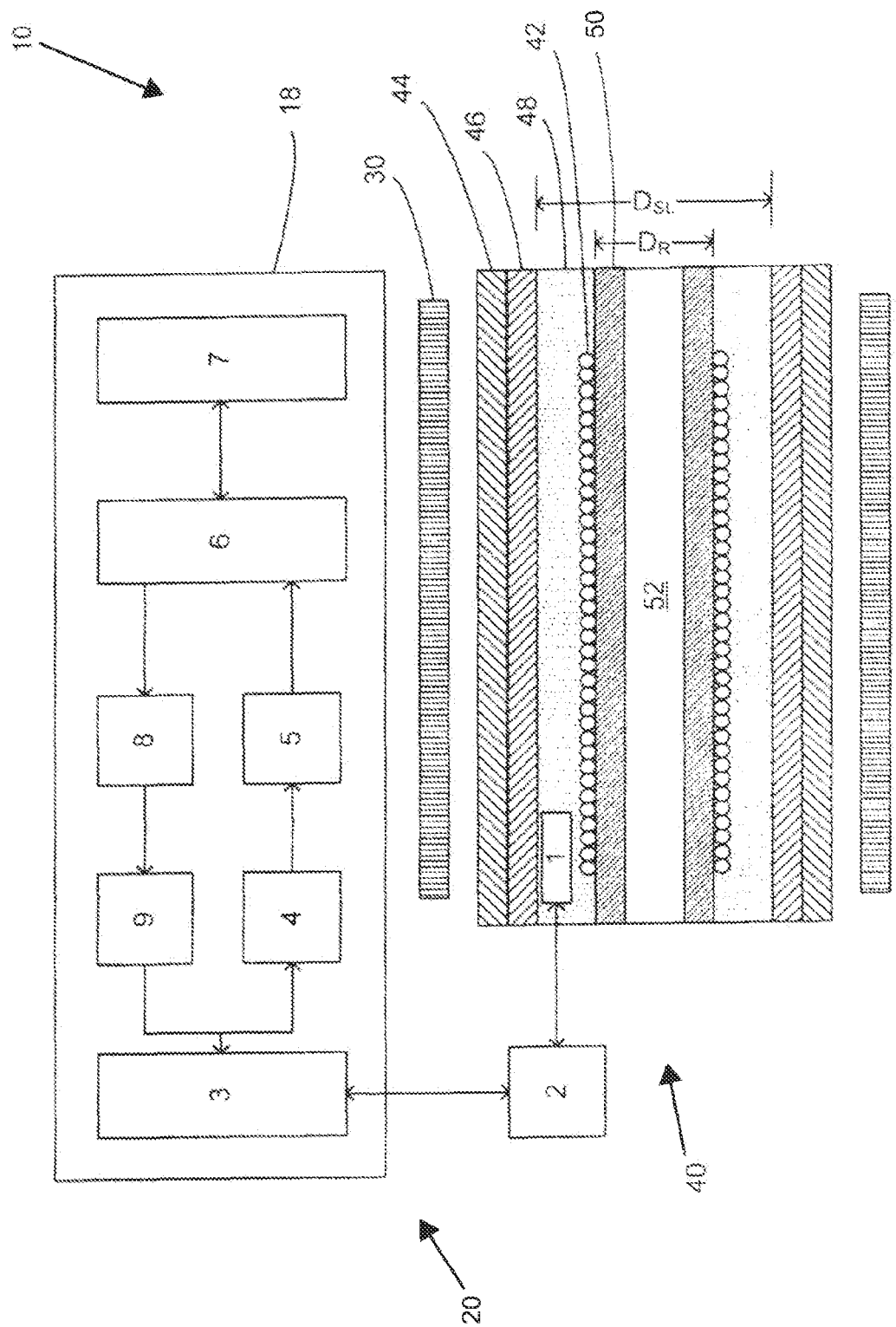
FIG. 1 is a schematic view of an NMR apparatus for use in an NMR instrument in accordance with one embodiment of the invention.
Figure 2:
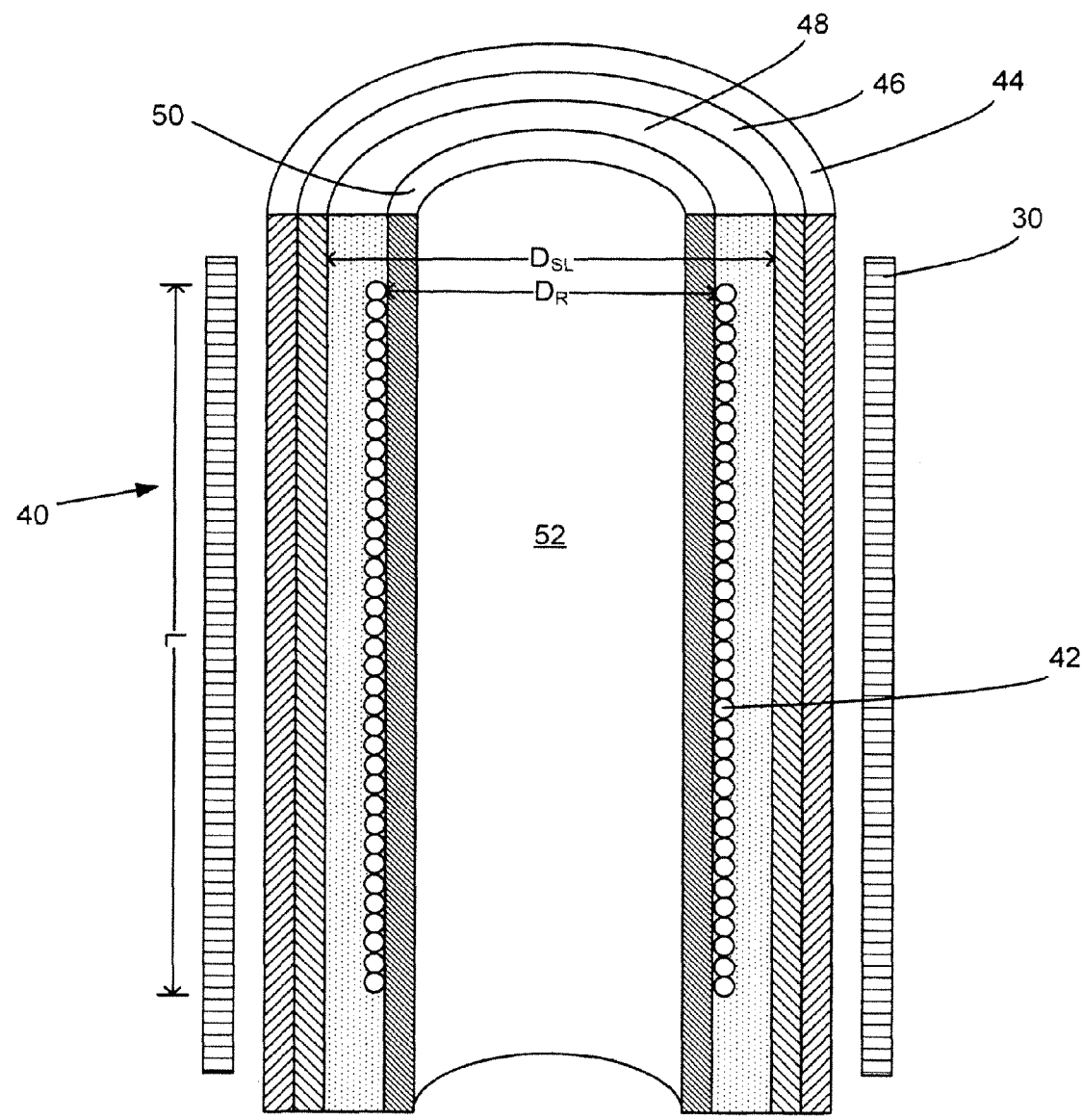
FIG. 2 is a cross-sectional view of an NMR compatible pipe in accordance with one embodiment of the invention.
Figure 2A:
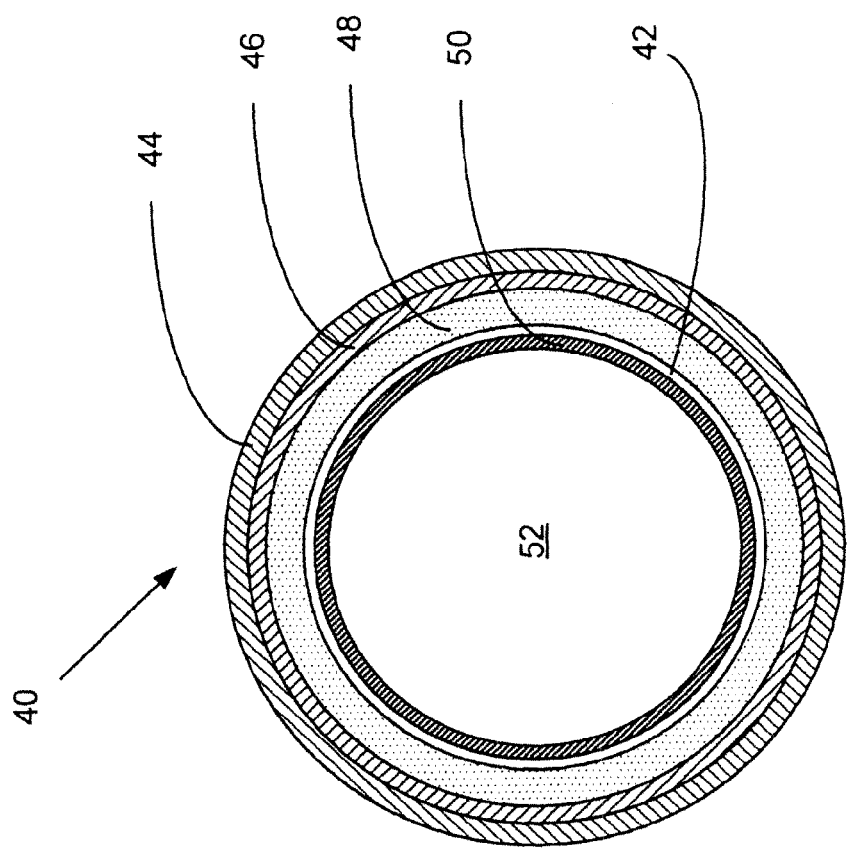
FIG. 2A is a schematic end view of an NMR pipe in accordance with one embodiment of the invention.

FIGS. 1, 2 and 2A illustrate the pipe 40 as having a resonator 42 located inside the NMR pipe for the transmission of a pulse sequence and NMR signal detection, and several layers including an outer layer 44, a shielding layer 46, a gap layer 48 and a core layer 50. An appropriate NMR magnet 30 surrounds the pipe 40 such as a permanent low field magnet (1-5 MHz).

As shown in FIGS. 1 and 3, to enable field-use and deployment, the apparatus 10 is secured to a skid 18b and further includes an electronic circuit 20 for generating and detecting the NMR signals. The electronic circuit preferably comprises a matching circuit 1, a preamplifier 2, a transceiver switch 3, an amplifier and filter 4, a data acquisition board 5, a computer/processor 6, a peripheral interface 7, a pulse forming board 8 and a transmitter 9. Preferably, various components of the electronic circuit 20 are enclosed in an explosion proof cabinet 18, shown in FIG. 1 and FIG. 3, in which an inside positive pressure is maintained preferably through the use of compressed air. A temperature control and purge unit 18c is located on the outside of the cabinet 18, along with a port 7b for the peripheral interface 7. First and second resistive thermal devices (RTDs) 54a, 54b are attached to the input and output ends of the pipe 40 to measure temperature.

As is known to those skilled in the art, the magnet 30 creates a strong, homogenous magnetic field that causes certain nuclei within the fluid sample 52 to line up within the magnetic field. The pulse forming board 8 provides pulsations of radiofrequency (RF) energy in a CPMG (Carr, Purcell, Meiboom and Gill) sequence that are transmitted to the resonator 42. The RF signal excites aligned molecules within the sample that then cause certain atomic nuclei to resonate. When the RF signal is turned off, the nuclei "relax" and produce a weak RF signal which induces a small current in the resonator coil that is received by the data acquisition board. The current is processed and analyzed by the processor to create NMR spectra for the sample using a standard NNLS (non-negative least-squares) algorithm. As atoms of different substances relax at different rates, it is possible to determine the relative amounts of particular atoms in the sample using NMR relaxometry analysis, of which methods are described below. In the preferred embodiment of the invention, hydrogen atoms are excited and hydrogen bearing molecules are detected.

Pipe Layers

The different layers of the pipe 40 are designed to maximize the signal-to-noise (SNR) ratio of the NMR instrument by maximizing the sample volume of the fluid 52 for a given diameter of pipe. In NMR, SNR is proportional to the square root of the quality factor (Q) of the resonator 42 and to the sample volume. It is preferable that the Q factor is optimized for SNR and for ringing time constant, which is proportional to Q. At some point of Q, ringing time (recovery time or dead time) is minimal in order to maximize SNR. As known to those skilled in the art, there are practical methods, such as active damping, that can be used to improve SNR while keeping recovery time minimal.

The non-magnetic outer layer 44 has mechanical characteristics designed to withstand the high temperatures and pressures that pipes used in oil and gas operations typically encounter. Suitable materials include stainless steel, beryllium, copper, and titanium. Preferably titanium (Grade 2 or Grade 5) is used, as a lesser thickness of titanium is required in comparison to beryllium, copper, and stainless steel to provide the necessary mechanical characteristics. The smaller wall thickness translates into a larger available volume inside the pipe for the sample fluid, which effectively increases the SNR of the instrument.

Located interior to the outer layer 44 is the shielding layer 46 that is designed to shield the resonator 42 from outside noise. The shielding layer is preferably made from the same material as the resonator 42, such as copper. Alternatively the shielding layer is manufactured from a non-magnetic material with a higher conductivity than the material of the resonator in order to maximize the Q factor of resonator 42. Table 1 below illustrates the ratio of the resonator diameter ($D_r$) to shielding layer diameter ($D_{sl}$) to maximize the Q factor of the resonator for a given shielding layer material.

TABLE 1

Ratio Of Resonator Coil Diameter ($D_r$) To Shielding Layer Diameter ($D_{sl}$) To Maximize The Q Factor For A Given Shielding Layer Material

| Shielding Layer Material | Relative high frequency effective resistance to copper | Best ratio of $D_r/D_{sl}$ to maximize Q factor of resonator |
|---|---|---|
| Super Conductor | 0 | 0.659 |
| Silver | 0.98 | 0.552 |
| Copper | 1 | 0.55 |
| Titanium | 5.06 | 0.369 |

Figure 4:
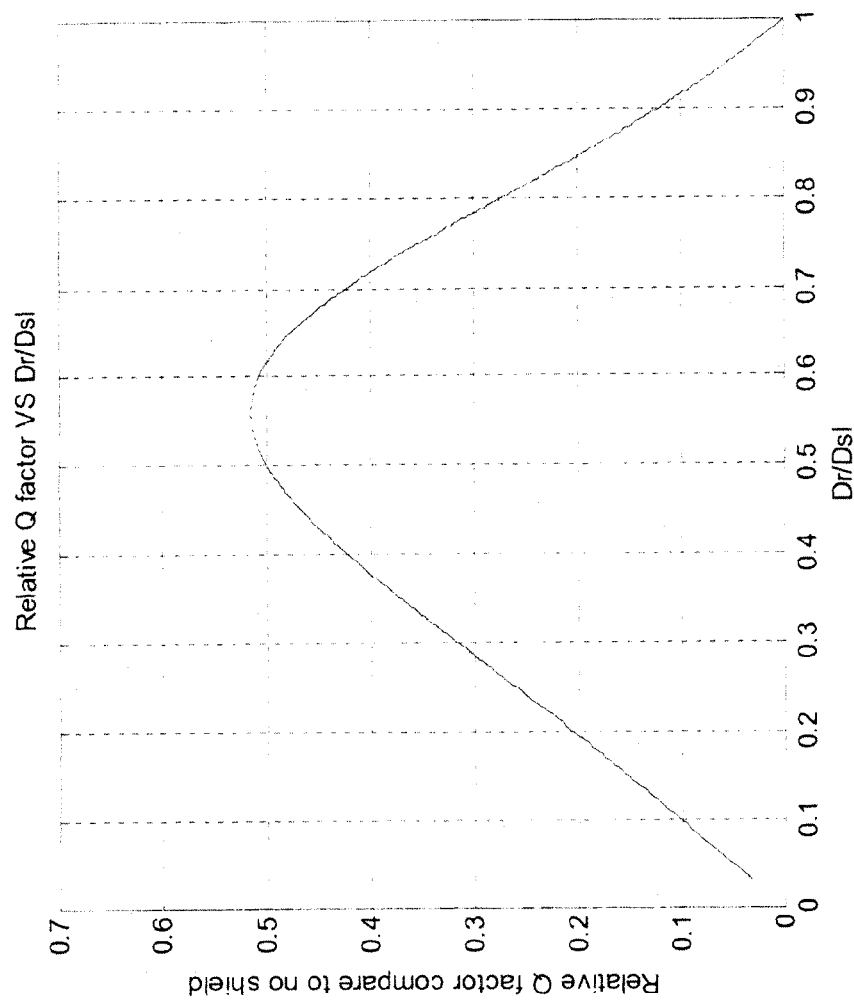
FIG. 4 is a graph of a relative quality factor (Q factor) of a resonator versus the ratio of the resonator diameter ($D_r$) and the ratio of an outer sleeve diameter ($D_{sl}$) of an NMR pipe in accordance with one embodiment of the invention.

As shown in FIG. 4, when the shielding layer 46 and the resonator 42 are made of the same material (e.g. copper), the ratio of the diameter of the resonator coil ($D_R$) and the diameter of the shielding layer ($D_{SL}$) are preferably optimized at about 0.55, which causes the resonator coil to have the highest Q factor for the limited volume available within the outer layer 44. Furthermore, it can also be seen in FIG. 4 that an increase in the resonator coil diameter in order to fit it into the available inner diameter of the outside conducting pipe, i.e. where the $D_R/D_{SL}$ ratio approaches 1, leads to a drastic drop in the Q value.

Interior of the shielding layer 46 is the gap or insulating layer 48 that creates a non-conductive space between the shielding layer and the innermost core layer 50 for optimum Q as shown in FIG. 4. The gap layer is filled with material in order to prevent flow of fluid on the outside of the resonator coil and to prevent the coil from mechanical wear. With this configuration, the gap layer also transfers the high pressure forces of a fluid sample within the pipe to the outer layer 44. Resins, as known to those skilled in the art, are suitable materials for the gap layer, as they are non-conductive and have sufficient mechanical strength. Another suitable material is polyetheretherketone (PEEK). The thickness of the gap layer 48 is defined by $(D_r-D_{sl})/2$.

The inner core layer 50 is a hollow cylinder for containing the fluid sample 52 within the inner core volume such that the fluid sample is in contact with the inner surfaces of the inner core layer. The inner core layer also provides support for the resonator 42 that is contained within the insulating layer. A suitable material for the core layer is polyetheretherketone (PEEK) which is non-metallic and has a high resistance to corrosion caused by a typical chemical environment of the fluid sample. Another suitable material for the inner core layer is Teflon®. It is preferable that the inner core layer 50 be made as thin as possible in order to maximize the sample volume; however the thinness of the inner core layer is restricted by factors including the abrasiveness of the fluids.

The resonator 42 is preferably a standard solenoid coil wrapped around the core layer that is immersed and contained within the gap layer 48. Preferably, the length L of the coil along the tube is at least twice the diameter of the coil which increases the homogenous radiofrequency (RF) field area inside the coil. It is preferable to use multiple wires connected in parallel which increases both the RF field homogeneity and the Q value of the coil.

Method for Determining Fluid Content

Methods for determining the properties of fluids, including the oil, water, solvent and gas content, at oil and gas well heads using NMR relaxometry are described. The measurements are taken in either stationary or flowing modes for the fluid.

Measurement of Oil and Water Content in a Stationary Fluid

Figure 5:
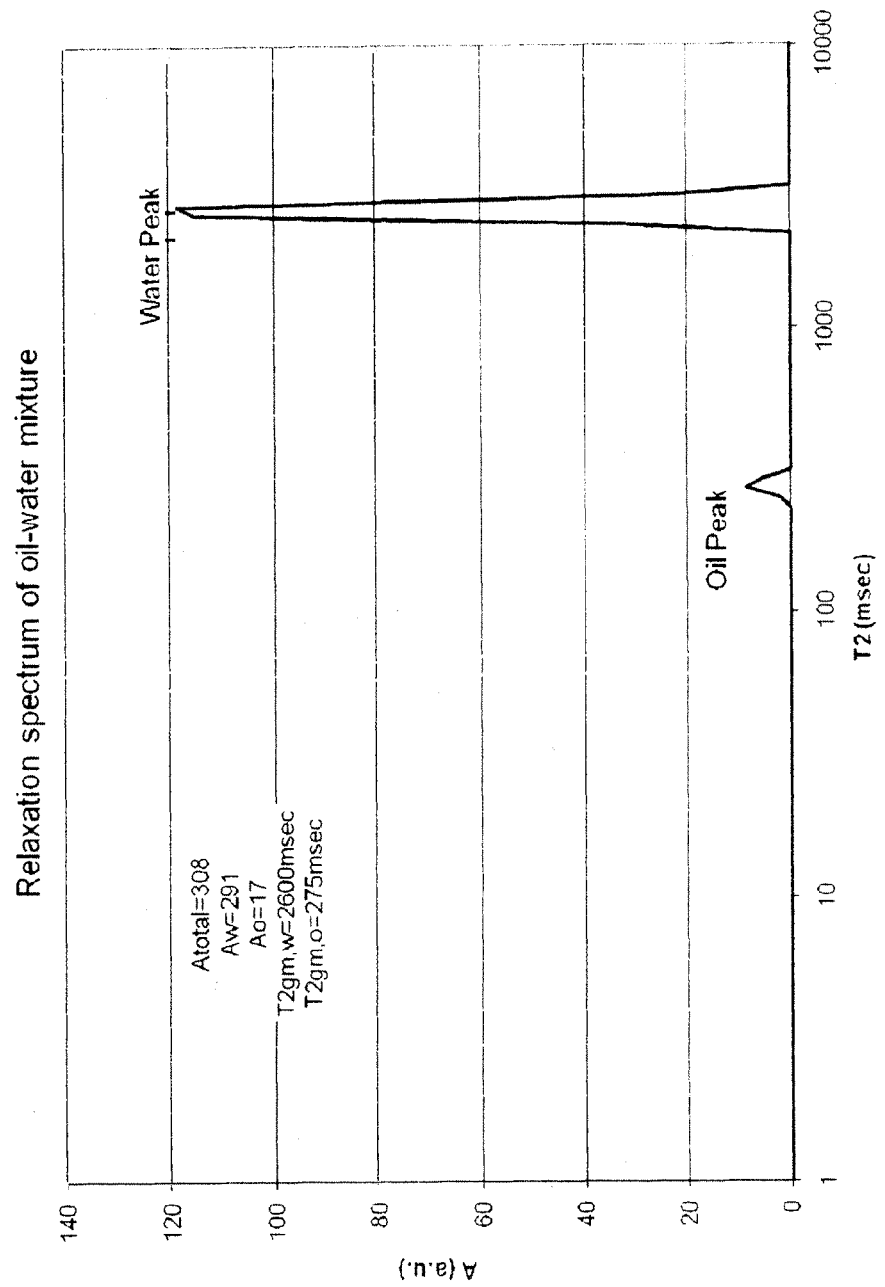
FIG. 5 is a graph of a relaxation spectrum of an oil and water mixture in accordance with one embodiment of the invention.

To determine the oil and water content of a stationary fluid in a pipe running through an NMR meter, a heavy oil (bitumen) and water signal are separated in the NMR T2 relaxation spectrum. The two measurements can be taken independently of each other. The graph in FIG. 5 illustrates a typical observed separation of oil and water peaks.

Assuming that the pipe is totally and uniformly filled with a mixture of oil and water (or radial sensitivity of NMR is uniform), the signal from water is proportional to the amount of water in the mixture in the following sense:

$$A_w(T,P) = \int AI_w(T,P,\vec{r}) \rho_w(T,P) S_w(\vec{r}) d^3\vec{r} \quad (1)$$

where T is temperature, P is pressure, $\vec{r}$ is a vector representing integration element position, $A_w(T,P)$ is total water amplitude, $AI_w(T,P,\vec{r})$ is water (mass) amplitude index, $\rho_w(T,P)$ is water density, and $S_w(\vec{r})$ is current water saturation (portion of the fluid volume element occupied by water). In the case of the uniform fluids distribution only $AI_w(T,P,\vec{r})$ is spatially dependent, then:

$$A_w(T,P) = \rho_w(T,P) S_w \int AI_w(T,P,\vec{r}) d^3\vec{r} \quad (2)$$

The amount of oil in the fluid can be determined by replacing water with oil in the above formulae.

Calibration of the system is performed with the pipe filled with water only based on the following:

$$A_{w,100\%}(T,P) = \rho_w(T,P) \int AI_w(T,P,\vec{r}) d^3\vec{r} \quad (3)$$

Water cut (volumetric) ($S_w$) within a cross-section of the pipe inside the magnetic field can be obtained according to the following relation:

$$S_w = \frac{A_w(T,P)}{A_{w,100\%}(T,P)} \quad (4)$$

As $S_w + S_o = 1$, then $S_o = 1 - S_w$.

Volumetric water cut can be converted into the mass water cut ($WC_m$) by the following:

$$WC_m = \frac{S_w \rho_w(T,P)}{S_w \rho_w(T,P) + S_o \rho_o(T,P)} \quad (5)$$

Radial variations of $AI_w(T,P,\vec{r})$ in a properly designed NMR relaxometer can be as low as 1% and even less. However, within the length of the measured volume of the pipe inhomogeneities of the magnetic field will exist. There may also be variations in water saturation along the length of the pipe if the system is flowing. To account for these variations, the above formulae become:

$$A_w(T,P) = \int AI_w(T,P,z) \rho_w(T,P) (\int S_w(x,y,z) dxdy) dz \quad (6)$$

or $$A_w(T,P) = \int AI_w(T,P,z) \rho_w(T,P) \overline{S}_w(z) dz \quad (7)$$

where $\bar{S}_w(z)=(\int S_w(x,y,z)dxdy)$ is water saturation averaged over the pipe cross-section. With the flow in the pipe stationary and settled, this value does not depend on z and again:

$$A_w(T,P)=\rho_w(T,P)\bar{S}_w \int AI_w(T,P,z)dz \qquad (8)$$

$$A_{w,100\%}(T,P)=\rho_w(T,P)\int AI_w(T,P,z)dz \qquad (9)$$

$$\bar{S}_w = \frac{A_w(T,P)}{A_{w,100\%}(T,P)} \qquad (10)$$

Measurement of Water and Gas Content in a Stationary Fluid

The last set of formulae can be applied to any two phase system present in the pipe. If it is known that the only phases present are gas and water then the above formulae still give the volumetric water saturation $S_w$ and volumetric gas saturation $S_g=1-S_w$. The mass gas-water ratio (GWR) can be established based on the equation of state of gas at the known pressure and temperature:

$$GWR = \frac{S_g \rho_g(T,P)}{S_w \rho_w(T,P)} \qquad (11)$$

Measurement of Oil and Gas Content in a Stationary Fluid

The above water-gas measurement procedure is directly transferable to oil-gas flows.

$$A_o(T,P) = \rho_o(T,P)\bar{S}_o \int AI_o(T,P,z)dz$$

$$A_{o,100\%}(T,P) = \rho_o(T,P)\int AI_o(T,P,z)dz$$

$$\bar{S}_o = \frac{A_o(T,P)}{A_{o,100\%}(T,P)}$$

It should be understood that the measurement of the value:

$$A_{o,100\%}(T,P)=\rho_o(T,P)\int AI_o(T,P,z)dz$$

for oil will require a sufficient amount of oil in order to perform a calibration procedure. As oil properties are subject to more variation than water properties, calibration procedures must occur more frequently.

Measurement of Oil, Water and Gas Content in a Stationary Fluid

In order to determine the oil, water and gas content of the flow, the measurements of oil and water signals in an appropriate range of relaxation times can be applied as follows:

$$A_w(T,P)=\rho_w(T,P)\bar{S}_w \int AI_w(T,P,z)dz$$

(Water)

$$A_o(T,P)=\rho_o(T,P)\bar{S}_o \int AI_o(T,P,z)dz$$

(Oil)

$$A_{o,100\%}(T,P)=\rho_o(T,P)\int AI_o(T,P,z)dz$$

(Pure Oil)

$$A_{w,100\%}(T,P)=\rho_w(T,P)\int AI_w(T,P,z)dz$$

(Pure Water)

Integration above is performed over the oil or water peak accordingly (see FIG. 5). Typically, the entire oil spectrum is below 300 ms and the water spectrum is above this threshold.

$$S_w = \frac{A_w(T,P)}{A_{w,100\%}(T,P)} \qquad (12)$$

$$S_o = \frac{A_o(T,P)}{A_{o,100\%}(T,P)} \qquad (13)$$

$$S_g = 1 - S_w - S_o \qquad (14)$$

Conversion of volume fractions into mass fractions can be performed as above with the use of PVT properties of each phase.

The instrument must be calibrated by filling the pipe with water (equations (3)/(9)) or oil (for oil equivalent of equation (9)). $A_{w,100\%}(T,P)$, $A_{o,100\%}(T,P)$ for the full range of operating temperatures and pressures is done prior to installation. If the produced water and oil do not chemically change during production, then this calibration is sufficient. However, in order to account for noise and changes in production fluid properties, bi-annual calibrations are preferable. If the instrument is move to a different production location recalibration is preferable.

Calibration Procedure for Oil

In order to minimize the frequency of performing the oil calibration procedure, the following alternate oil calibration procedure can be performed.

For three phase measurements, the $A_{o,100\%}(T,P)$ may be difficult to obtain. If the system can be operated in two-phase mode without gas then the following calibration can be made. The system is run in two-phase mode (no gas) and measurements are taken. For the flow without a gas phase $S_o+S_w=1$. With the use of previous relations this can be represented as $$\frac{A_w(T,P)}{A_{w,100\%}(T,P)} + \frac{A_o(T,P)}{A_{o,100\%}(T,P)} = 1 \qquad (15)$$

$A_{w,100\%}(T,P)$ is a relatively simple function to measure in the laboratory. Then the following equation will be applicable:

$$A_{o,100\%}(T,P) = A_{w,100\%}(T,P)\frac{A_o(T,P)}{A_{w,100\%}(T,P) - A_w(T,P)} \qquad (16)$$

The above relation allows for the extraction of the unknown function $A_{o,100\%}(T,P)$ that can be used in three phase measurements later.

Measurement of Oil and Water Content in a Continuous Flow

The above water-oil measurement procedure can be adapted for continuous oil-water flow if only the oil component is tracked in velocities that allow collection of the oil relaxation signal without counting for the water relaxation signal.

$$A_o(T,P) = \rho_o(T,P)\bar{S}_o \int AI_o(T,P,z)dz$$

$$A_{o,100\%}(T,P) = \rho_o(T,P)\int AI_o(T,P,z)dz$$

$$S_o = \frac{A_o(T,P)}{A_{o,100\%}(T,P)}$$

It should be understood that the measurement of the value:

$$A_{o,100\%}(T,P)=\rho_o(T,P)\int AI_o(T,P,z)dz$$

for oil will require a sufficient amount of oil in order to perform calibration procedure. As oil properties are subject to more variation than water properties this will mean more often calibration procedures. The water signal is calculated as: $S_w = 1 - S_o$

FIELD TRIALS/EXAMPLES

Figure 6:
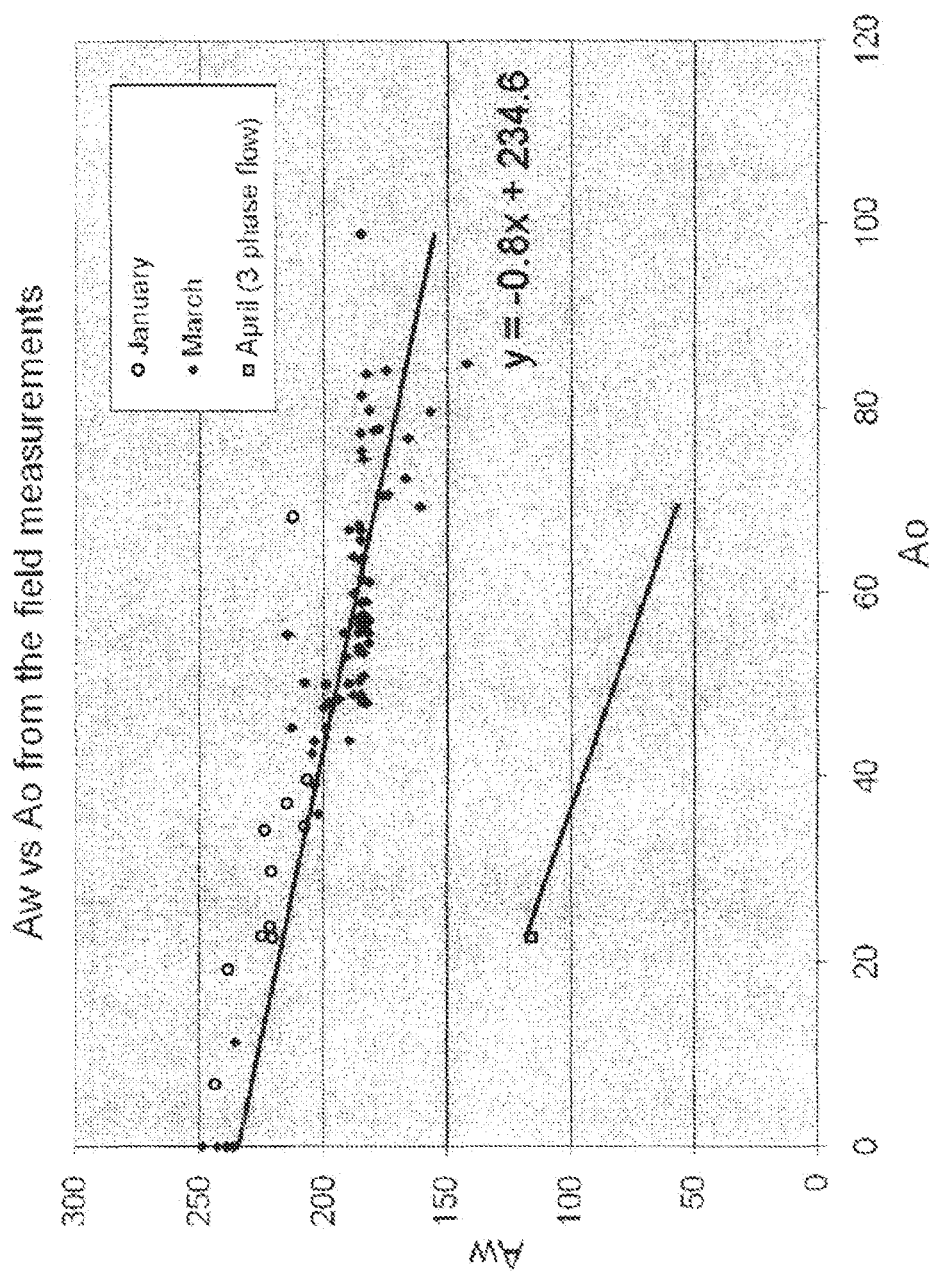
FIG. 6 is a graph of total water amplitude versus total oil amplitude for field measurements performed in accordance with one embodiment of the invention.

The graph in FIG. 6 presents field trial measurements for the NMR apparatus and method. As seen, the data fall closely on a straight line according to the relation as shown in Equation 16.

Table 2 shows a comparison of the NMR field data compared to Dean-Stark (lab) measurements for the same samples. The sample was split into two samples for the Dean-Stark measurements.

TABLE 2

A Comparison of NMR and Dean-Stark (DS) Water Cut (WC) Measurements For Four Samples.

| Sample # | WC from DS (%) | WC from NMR (%) |
|---|---|---|
| 1a | 82.85 | 82.4 |
| 1b | 82.77 | |
| 2a | 78.95 | 80.2 |
| 2b | 80.29 | |

Accordingly, the results show good correlation between the field measured and laboratory analysis samples.

Although the present invention has been described and illustrated with respect to preferred embodiments and preferred uses thereof, it is not to be so limited since modifications and changes can be made therein which are within the full, intended scope of the invention as understood by those skilled in the art.

The invention claimed is:

1. A pipe system for enabling nuclear magnetic resonance (NMR) analysis of gas and liquids within the pipe system comprising:
   an inner layer defining an internal volume within the pipe;
   an insulating layer in operative contact with the inner layer, the insulating layer containing and supporting an NMR resonator coil;
   a shielding layer in operative contact with the insulating layer; and
   an outer non-magnetic layer in operative contact with the shielding layer for operatively containing pressurized fluids within the inner layer.

2. The pipe system as in claim 1 wherein the outer non-magnetic layer is selected from any one of or a combination of titanium, stainless steel, beryllium, and copper.

3. The pipe system as in claim 1 wherein a ratio of a diameter of the NMR resonator coil and a diameter of the shielding layer ($D_R/D_{SL}$) is between 0.3 and 0.7.

4. The pipe system as in claim 1 wherein the shielding layer is selected from any one of or a combination of silver, copper, titanium and a superconductor.

5. The pipe system as in claim 1 wherein the insulating layer is a resin.

6. A nuclear magnetic resonance (NMR) system comprising:
   a low field (1-5 MHz) permanent magnet operatively configured to a pipe system, the pipe system comprising an inner layer defining an internal volume within the pipe;
   an insulating layer in operative contact with the inner layer, the insulating layer containing and supporting an NMR resonator coil;
   a shielding layer in operative contact with the insulating layer; and
   an outer non-magnetic layer in operative contact with the shielding layer for operatively containing pressurized fluids within the inner layer;
   a pulse signal creation circuit operatively connected to the NMR resonator coil for generating radiofrequency (RF) pulsations to the NMR resonator coil;
   an RF receiver circuit for receiving and filtering RF data from the pipe system for delivery to a data acquisition system;
   a transceiver switch circuit operatively connected to the pulse signal creation circuit and RF receiver circuit for operative switching between a signal creation and a signal listening mode; and
   an explosion proof container for operative containment of the magnet, pulse signal creation circuit, RF receiver circuit and transceiver switch circuit.

7. A system as in claim 6 further comprising an air purge cooling system for maintaining a positive pressure within the explosion proof container.

8. A pipe system for enabling nuclear magnetic resonance (NMR) analysis of gas and liquids within the pipe system comprising:
   an inner layer defining an internal volume within the pipe;
   a thermoplastic insulating layer in operative contact with the inner layer, the thermoplastic insulating layer containing and supporting an NMR resonator coil;
   a shielding layer selected from any one or a combination of silver, copper, titanium and a superconductor, in operative contact with the thermoplastic insulating layer; and
   an outer non-magnetic layer selected from any one of or a combination of titanium, stainless steel, beryllium and copper, in operative contact with the shielding layer for operatively containing pressurized fluids within the inner layer.

9. The pipe system as in claim 8 wherein the outer non-magnetic layer is titanium.

10. The pipe system as in claim 8 wherein the shielding layer is copper.

11. The pipe system as in claim 8 wherein a ratio of a diameter of the NMR resonator coil and a diameter of the shielding layer ($D_R/D_{SL}$) is between 0.5 and 0.6.

12. The pipe system as in claim 8 wherein the shielding layer is titanium.

13. The pipe system as in claim 8 wherein a ratio of a diameter of the NMR resonator coil and a diameter of the shielding layer ($D_R/D_{SL}$) is between 0.3 and 0.4.

14. The pipe system as in claim 8 wherein the thermoplastic insulating layer is polyetheretherketone (PEEK).

15. The pipe system as in claim 8 wherein the NMR resonator coil is copper.

16. The pipe system as in claim 8 wherein the NMR resonator coil is the same material as the shielding layer.

17. The pipe system as in claim 8 wherein the thermoplastic insulating layer has a higher conductivity than the NMR resonator coil.

18. The pipe system as in claim 8 wherein the inner layer is polyetheretherketone (PEEK).

19. The pipe system as in claim 8 wherein the inner layer is polytetrafluoroethylene.

20. The pipe system as in claim 8 wherein a length of the NMR resonator coil along the pipe is greater than twice a diameter of the resonator coil.

21. The pipe system as in claim 8 wherein the NMR resonator coil comprises a plurality of coils connected in parallel.

22. A pipe system for enabling nuclear magnetic resonance (NMR) analysis of gas and liquids within the pipe system comprising:
- an inner layer composed of polyetheretherketone (PEEK) defining an internal volume within the pipe;
- a thermoplastic insulating layer made of polyetheretherketone (PEEK) in operative contact with the inner layer, the insulating layer containing and supporting an NMR resonator coil made of copper;
- a shielding layer made of titanium, in operative contact with the insulating layer; and
- an outer non-magnetic layer made from titanium in operative contact with the shielding layer for operatively containing pressurized fluids within the inner layer.

\* \* \* \* \*